(12) United States Patent
Nielsen et al.

(10) Patent No.: US 8,637,580 B2
(45) Date of Patent: Jan. 28, 2014

(54) PROCESS FOR THE PREPARATION OF ETHANOL AND HIGHER ALCOHOLS

(75) Inventors: Poul Erik Højlund Nielsen, Fredensborg (DK); Burcin Temel, Hellerup (DK); Pablo Beato, Copenhagen S (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 13/808,240

(22) PCT Filed: May 17, 2011

(86) PCT No.: PCT/EP2011/002447
§ 371 (c)(1),
(2), (4) Date: Jan. 3, 2013

(87) PCT Pub. No.: WO2012/003901
PCT Pub. Date: Jan. 12, 2012

(65) Prior Publication Data
US 2013/0123377 A1 May 16, 2013

(30) Foreign Application Priority Data
Jul. 5, 2010 (DK) .................................. 2010 00595

(51) Int. Cl.
*C07C 27/00* (2006.01)

(52) U.S. Cl.
USPC ............ 518/713; 518/700; 518/714; 518/715

(58) Field of Classification Search
USPC .................................. 518/700, 713, 714, 715
See application file for complete search history.

(56) References Cited

U.S. PATENT DOCUMENTS

| 2,468,510 A * | 4/1949 | Owen ........................... 518/705 |
| 4,825,013 A | 4/1989 | Quarderer et al. |
| 2009/0018371 A1 | 1/2009 | Klepper et al. |

FOREIGN PATENT DOCUMENTS

EP  0 499 095 A1  8/1992

\* cited by examiner

*Primary Examiner* — Jafar Parsa
(74) *Attorney, Agent, or Firm* — Dickstein Shapiro LLP

(57) ABSTRACT

Process for the preparation of ethanol and/or higher alcohols comprising the steps of: (a) providing an alcohol synthesis gas comprising carbon monoxide and hydrogen in a molar ratio of higher than 0.5; (c) adding an amount of methanol and/or higher alcohols to the synthesis gas to obtain a synthesis gas mixture. (d) converting the synthesis gas mixture from step (c) in presence of one or more catalysts catalysing the conversion of the synthesis gas mixture into a ethanol and/or higher alcohols containing product; and (e) withdrawing the product from step (d), wherein the synthesis gas is purified by removing iron and nickel carbonyl compounds prior or after the addition methanol and/or higher alcohols to the synthesis gas and optionally (I) cooling the withdrawn product in step (e); and (g) contacting the cooled product with a hydrogenation catalyst.

10 Claims, No Drawings

PROCESS FOR THE PREPARATION OF ETHANOL AND HIGHER ALCOHOLS

The present invention relates to the production of ethanol or higher alcohols. In particular the invention is a process for the preparation of these alcohols by conversion of carbon monoxide and hydrogen containing synthesis gas admixed with ethanol in presence of a catalyst containing oxides of copper, zinc and aluminium.

It is known that higher alcohols and other oxygenates are formed as by-product in the catalytic methanol synthesis from synthesis gas.

It is also known that higher alcohol products can be produced directly from synthesis gas.

U.S. patent application no. 2009/0018371 discloses a method for the producing alcohols from synthesis gas. The synthesis gas is in a first step partially converted to methanol in presence of a first catalyst and in a second step methanol is converted with a second amount of synthesis gas to a product comprising C2-C4 alcohols in presence of a second catalyst. The second amount of synthesis gas can include unreacted synthesis gas from the first step.

The alcohol synthesis requires a high concentration of carbon monoxide in the synthesis gas. A useful synthesis gas has a CO/H2 ratio of at least 0.5. The synthesis gas for the higher alcohol synthesis is prepared by the well known steam reforming of liquid or gaseous hydrocarbons or by means of gasification carbonaceous material, like coal, heavy oil or bio mass.

When using an oxidic alcohol formation catalyst together with a synthesis gas having a high content of carbon monoxide, the catalyst has a relatively short operation time. The catalyst bed will after a time on stream be clogged with waxy material and has to be removed.

We have found that this problem arises during preparation of the synthesis gas under conditions to provide a relatively high content of carbon monoxide. Carbon monoxide reacts with the steel equipment used in the synthesis gas preparation and forms inter alia iron carbonyl compounds. When transferred to the alcohol synthesis catalyst, these compounds catalyse the Fischer-Tropsch reaction and the waxy material is formed on the catalyst.

By removing the carbonyl compounds from the synthesis gas upstream of the alcohol synthesis, the operation time of the catalyst can be much improved.

It has further been found that addition of methanol and in particular alcohols higher than methanol to the synthesis gas results in a drastic increase in the yield of higher alcohols when compared to the known methanol synthesis gas mixture.

Pursuant to the above findings, this invention is a process for the preparation of ethanol and/or higher alcohols comprising the steps of:
(a) providing an alcohol synthesis gas comprising carbon monoxide and hydrogen in a molar ratio of higher than 0.5;
(c) adding an amount of methanol and/or higher alcohols to the synthesis gas
(d) converting the synthesis gas mixture from step (c) in presence of one or more catalysts catalysing the conversion of the synthesis gas mixture into a ethanol and/or higher alcohols containing product; and
(e) withdrawing the product from step (d), wherein the synthesis gas is purified by removing metal carbonyl compounds prior or after the addition methanol and/or higher alcohols to the synthesis gas.

As used hereinbefore and in the following description and the claims, the term "higher alcohols" refers to ethanol and alcohols having more than 2 carbon atoms.

Catalysts being active in the conversion of synthesis gas to higher alcohols are per se known in the art. For use in the present invention a preferred catalyst consists of copper, zinc oxide and aluminium oxide and optionally promoted with one or more metals selected from alkali metals, basic oxides of earth alkali metals and lanthanides being commercially available from Haldor Topsøe A/S, Denmark.

As already discussed above, an essential feature of this invention is the removal of metal carbonyl compounds, in particular iron and nickel carbonyl, from the synthesis gas in order to prevent formation of waxy material on the alcohol preparation catalyst due to the Fischer-Tropsch reaction catalysed by metal carbonyl compounds being otherwise present in the synthesis gas.

A particular useful metal carbonyl sorbent for use in the inventive process comprises copper aluminium spinel being modified by calcination at elevated temperature in an oxidizing atmosphere followed by a reduction in a reducing atmosphere, such as synthesis gas or synthesis gas diluted with an inert gas, prior to being contacted with metal carbonyl contaminated synthesis gas.

Copper aluminum spinels are per se known compounds and the preparation of copper aluminum spinel is described in the art e.g. Z. Phys. Chem., 141 (1984), 101-103.

Preferably, the particulate sorbent further comprises copper oxide in excess to the amount being present in the copper aluminum spinel prior to modification.

A typical preparation method comprises co-precipitation of copper and aluminum salts and calcination in air at a temperature of between 700° C. and 900° C. to form crystals with the spinel structure.

These sorbents remove carbonyl compounds from the synthesis gas to the low ppb range, preferably below 1 ppb.

The sorbent may be arranged as an isothermal guard reactor in front of the alcohol synthesis reactor or as top layer on a fixed catalyst with the one or more catalysts catalysing the conversion of the synthesis gas.

The absorber is effective at inlet temperature of the alcohol synthesis gas mixture of between 200 to 250° C. Therefore it is preferred to place the absorbent directly on top of the alcohol preparation catalyst bed instead of having a separate absorber reactor, which would also imply a cooling and/or heating step of the synthesis gas prior to introduction into the alcohol reactor.

A further essential feature of the invention is the addition of methanol and/or higher alcohols to the synthesis gas upstream the alcohol reactor in order to increase the production yield of desired higher alcohols. Addition of only methanol, slightly improves the formation of higher alcohols. The prime reason for adding methanol is to control the temperature in the catalyst bed.

Methanol formation is an exothermic process and low methanol content in the gas will give rise to a drastic temperature increase at reactor inlet. Thus by adding methanol in an amount, which adjusts the reaction mixture to the thermodynamic equilibrium with respect to the content of methanol in the synthesis reaction, no methanol formation will take place at reactor inlet.

As synthesis gas is consumed in the reactor due to formation of higher alcohols an amount of the methanol will be decomposed. Methanol decomposition is an endothermic reaction that provides an improved temperature control in the catalyst bed. Alcohols like ethanol and propanol participate in the synthesis of higher alcohol resulting in a large increase of the rate of formation of higher alcohols.

It is therefore preferred to add a mixture of methanol and higher alcohols to the synthesis gas.

The alcohols may be admixed in the liquid phase into the synthesis gas upstream the alcohol reactor and evaporate subsequently in the synthesis gas.

The synthesis of higher alcohols is preferably carried out at a pressure of at least 2 MPa, typically between 2 and 15 MPa and a temperature above 250° C., preferably between 270 and 330° C.

The alcohol synthesis can be performed in an adiabatic operated reactor with quench cooling or preferably in a cooled boiling water reactor, producing high pressure steam. In the boiling water reactor large diameter tubes may be used due to the modest reaction rate.

In the synthesis of higher alcohols small amounts of aldehydes and ketons together with other oxygenates are formed as by-products. These by-products may form azetropic mixtures with the higher alcohols or have boiling points close to the alcohols and leave the purification of the product difficult.

In a specific embodiment of the invention, the alcohol product being withdrawn from the alcohol synthesis step is subjected to a hydrogenation step in presence of a hydrogenation catalyst, wherein the oxygenate by-products are hydrogenated to their corresponding alcohols. Thereby, the final distillation of the product is much improved.

For the purpose of the product hydrogenation, the alcohol product being withdrawn from the alcohol synthesis is cooled in a feed effluent heat exchanger to a temperature between 100 and 200° C. and introduced into a hydrogenation reactor containing a bed of hydrogenation catalyst. Useful hydrogenation catalysts are catalysts containing noble metals including platinum and palladium or a copper/zinc oxide/alumina catalyst being also employed in the alcohol synthesis.

The thus treated alcohol product is passed to a distillation step, wherein water and a part of the higher alcohols are separated from the remaining higher alcohols. The separated amount of is admixed into the purified synthesis gas as described hereinbefore.

EXAMPLES

Example 1

Alkali modified (1 wt. % K) alcohol preparation catalyst consisting of oxides of copper, zinc and aluminium (commercially available from Haldor Topsoe A/S under the trade name "MK-121") is activated at 1 bar, with a 4000 Nl/h/kg·cat space velocity of 3% $H_2$, 0.2% CO, 4.4% $CO_2$ in $N_2$ gas mixture starting at 170° C. and heating up to 225° C. with a 10° C./min ramp. It is kept at 225° C. for two hours. The thus activated catalyst consists of metallic copper, zinc oxide and aluminium oxide, promoted with potassium carbonate.

The catalyst evaluation experiments were carried out in a copper lined stainless steel plug-flow reactor (19 mm ID) containing catalyst pellets (20-50 g, pellet diameter 6 mm and height 4 mm) held in place by quartz wool.

The reactor effluent was analyzed by on-line gas chromatograph. The liquid composition was identified with a GC-MS.

The reaction temperature, gas composition, alcohol co-feeding, space velocity and pressure effects were evaluated and the results are shown in Tables 1-5 below. The synthesis gas mixture contained $H_2$ and CO (with the specified ratios in the Tables), 2-5 vol. % $CO_2$ and 3 vol. % Ar.

TABLE 1

Effect of temperature on the higher alcohols production:
$H_2/CO$ = 1.1, 80 bar, SV = 2000 Nl/kg · cat/h, 20 g catalyst.

| Temperature (° C.) | 280 | 300 | 320 |
|---|---|---|---|
| MeOH (inlet, g/h) | 16.461 | 9.369 | 5.121 |
| CO % conversion | 13 | 22 | 29 |
| Exit composition (g/h/g · cat) | | | |
| Methanol | 0.8486 | 0.4681 | 0.2671 |
| Ethanol | 0.0194 | 0.0191 | 0.0120 |
| 1-Propanol | 0.0130 | 0.0206 | 0.0163 |
| 2-Propanol | 0.0009 | 0.0022 | 0.0021 |
| 2-Methyl-1-propanol | 0.0004 | 0.0219 | 0.0303 |
| Other butanols | 0.0047 | 0.0065 | 0.0050 |
| Pentanols | 0.0050 | 0.0111 | 0.0110 |
| Hexanols and higher | 0.0024 | 0.0054 | 0.0061 |
| Total (Ethanol and higher) | 0.0458 | 0.0867 | 0.0828 |

TABLE 2

Effect of module on the higher alcohols production:
T = 320° C., 80 bar, SV = 2000 Nl/kg · cat/h, 20 g catalyst.

| Module ($H_2/CO$) | 0.5 | 1.1 |
|---|---|---|
| MeOH (inlet, g/h) | 3.2240 | 5.1210 |
| CO % conversion | 31 | 29 |
| Exit composition (g/h/g · cat) | | |
| Methanol | 0.0879 | 0.2671 |
| Ethanol | 0.0038 | 0.0120 |
| 1-Propanol | 0.0068 | 0.0163 |
| 2-Propanol | 0.0021 | 0.0021 |
| 2-Methyl-1-propanol | 0.0233 | 0.0303 |
| Other butanols | 0.0028 | 0.0050 |
| Pentanols | 0.0088 | 0.0110 |
| Hexanols and higher | 0.0074 | 0.0061 |
| Total (Ethanol and higher) | 0.0550 | 0.0828 |

TABLE 3

Effect of pressure on the higher alcohols production:
T = 320° C., $H_2/CO$ = 0.5, SV = 2000 Nl/kg · cat/h, 20 g catalyst.

| Pressure (bar) | 80 | 100 |
|---|---|---|
| MeOH (inlet, g/h) | 3.2240 | 4.6070 |
| CO % conversion | 31 | 30 |
| Exit composition (g/h/g · cat) | | |
| Methanol | 0.0879 | 0.1449 |
| Ethanol | 0.0038 | 0.0071 |
| 1-Propanol | 0.0068 | 0.0123 |
| 2-Propanol | 0.0021 | 0.0034 |
| 2-Methyl-1-propanol | 0.0233 | 0.0347 |
| Other butanols | 0.0028 | 0.0041 |
| Pentanols | 0.0088 | 0.0122 |
| Hexanols and higher | 0.0074 | 0.0077 |
| Total (Ethanol and higher) | 0.0550 | 0.0815 |

TABLE 4

Effect of space velocity on the higher alcohols production:
T = 320° C., $H_2/CO$ = 1.1, 80 bar, 20 g catalyst.

| SV (Nl/h/kg · cat) | 2000 | 5000 | 10000 | 15000 |
|---|---|---|---|---|
| MeOH (inlet, g/h) | 5.1210 | 12.6820 | 25.4590 | 37.6670 |
| CO % conversion | 13 | 13 | 6 | 3 |

TABLE 4-continued

Effect of space velocity on the higher alcohols production:
T = 320° C., $H_2$/CO = 1.1, 80 bar, 20 g catalyst.

| Exit composition (g/h/g · cat) | | | | |
|---|---|---|---|---|
| Methanol | 0.2671 | 0.4991 | 1.0196 | 1.5475 |
| Ethanol | 0.0120 | 0.0190 | 0.0309 | 0.0369 |
| 1-Propanol | 0.0163 | 0.0227 | 0.0314 | 0.0329 |
| 2-Propanol | 0.0021 | 0.0023 | 0.0029 | 0.0027 |
| 2-Methyl-1-propanol | 0.0303 | 0.0349 | 0.0389 | 0.0345 |
| Other butanols | 0.0050 | 0.0063 | 0.0089 | 0.0092 |
| Pentanols | 0.0110 | 0.0138 | 0.0171 | 0.0159 |
| Hexanols and higher | 0.0061 | 0.0066 | 0.0079 | 0.0072 |
| Total (Ethanol and higher) | 0.0828 | 0.1056 | 0.1380 | 0.1393 |

TABLE 5

Effect of methanol addition on the higher alcohols
production: T = 320° C., $H_2$/CO = 1.1, 80 bar,
SV = 5000 Nl/h/kg · cat, 20 g catalyst.

| MeOH (inlet, g/h) | 12.6820 | — |
|---|---|---|
| CO % conversion | 29 | 25 |

| Exit composition (g/h/g · cat) | | |
|---|---|---|
| Methanol | 0.4991 | 0.3789 |
| Ethanol | 0.0190 | 0.0139 |
| 1-Propanol | 0.0227 | 0.0174 |
| 2-Propanol | 0.0023 | 0.0019 |
| 2-Methyl-1-propanol | 0.0349 | 0.0293 |
| Other butanols | 0.0063 | 0.0049 |
| Pentanols | 0.0138 | 0.0110 |
| Hexanols and higher | 0.0066 | 0.0053 |
| Total (Ethanol and higher) | 0.1056 | 0.0837 |

Example 2

Co-feeding ethanol or 1-propanol together with methanol and synthesis gas mixture. 50 grams of 1% wt. K/MK-121 were used as alcohol preparation catalyst.

TABLE 6

Effect of ethanol co-feeding with methanol and synthesis
gas on the higher alcohols production: T = 320° C.,
H2/CO = 0.5, 100 bar, SV = 2000 Nl/h/kg · cat, 50 g catalyst.

| EtOH (inlet, g/h) | | 11.4210 | 57.7630 | 115.9640 |
|---|---|---|---|---|
| MeOH (inlet, g/h) | 4.6070 | 11.9150 | 12.0500 | 12.1020 |
| CO % conversion | 29 | 31 | 36 | 27 |

| Exit composition (g/h/g · cat) | | | | |
|---|---|---|---|---|
| Methanol | 0.1449 | 0.1756 | 0.1882 | 0.0859 |
| Ethanol | 0.0071 | 0.0391 | 0.4776 | 1.3753 |
| 1-Propanol | 0.0123 | 0.0510 | 0.1533 | 0.1195 |
| 2-Propanol | 0.0034 | 0.0068 | 0.0061 | 0.0077 |
| 2-Methyl-1-propanol | 0.0347 | 0.0718 | 0.0384 | 0.0163 |
| Other butanols | 0.0041 | 0.0135 | 0.0707 | 0.1427 |
| Pentanols | 0.0122 | 0.0223 | 0.0456 | 0.0621 |
| Hexanols and higher | 0.0077 | 0.0198 | 0.0087 | 0.0054 |
| Total (excluding methanol and ethanol) | 0.0815* | 0.1852 | 0.3228 | 0.3536 |

TABLE 7

Effect of propanol co-feeding with methanol and synthesis
gas on the higher alcohols production: T = 320° C.,
H2/CO = 0.5, 100 bar, SV = 2000 Nl/h/kg · cat, 50 g catalyst.

| 1-Propanol (inlet, g/h) | | 15.2951 | 75.4682 | 151.2269 |
|---|---|---|---|---|
| MeOH (inlet, g/h) | 4.6070 | 12.2289 | 12.0718 | 12.0851 |
| CO % conversion | 29 | 23 | 20 | 14 |

| Exit composition (g/h/g · cat) | | | | |
|---|---|---|---|---|
| Methanol | 0.1449 | 0.2065 | 0.1985 | 0.1967 |
| Ethanol | 0.0071 | 0.0097 | 0.0034 | 0.0000 |
| 1-Propanol | 0.0123 | 0.1242 | 1.0580 | 2.6481 |
| 2-Propanol | 0.0034 | 0.0131 | 0.0033 | 0.0097 |
| 2-Methyl-1-propanol | 0.0347 | 0.1651 | 0.2253 | 0.0464 |
| Other butanols | 0.0041 | 0.0022 | 0.0042 | 0.0041 |
| Pentanols | 0.0122 | 0.0194 | 0.0913 | 0.1684 |
| Hexanols and higher | 0.0077 | 0.0229 | 0.0395 | 0.0493 |
| Total (excluding methanol and 1-propanol) | 0.0815* | 0.2325 | 0.3670 | 0.2780 |

*This value excludes only methanol.

Example 3

Post hydrogenation of unsaturated intermediates (aldehydes and ketones) to further alcohols: The plug flow reactor was loaded with higher alcohols catalyst (20 g) at the top part and a copper based hydrogenation catalyst (MK-121, 20 g) at the bottom part. The catalysts were treated initially same as described above.

TABLE 8

Effect of hydrogenation of the unsaturated intermediates on
the higher alcohols production: T = 300° C., H2/CO = 0.5,
80 bar, SV = 2000 Nl/h/kg · cat, 20 g higher alcohols +
20 g hydrogenation catalyst.

| Hydrogenation | yes | No |
|---|---|---|
| MeOH (inlet, g/h) | 4.616 | 8.8090 |
| CO % conversion | 35 | 31 |

| Exit composition (g/h/g · cat) | | |
|---|---|---|
| Methanol | 0.3231 | 0.3196 |
| Ethanol | 0.0093 | 0.0151 |
| 1-Propanol | 0.0138 | 0.0202 |
| 2-Propanol | 0.0034 | 0.0037 |
| 2-Methyl-1-propanol | 0.0265 | 0.0281 |
| Other butanols | 0.0042 | 0.0064 |
| Pentanols | 0.0100 | 0.0116 |
| Hexanols and higher | 0.0086 | 0.0066 |
| Total (Ethanol and higher) | 0.0758 | 0.0918 |

TABLE 9

Effect of Space Velocity (SV) with post hydrogenation on
the higher alcohols production: T = 300° C., H2/CO = 0.5,
100 bar, 20 g higher alcohols + 20 g
hydrogenation catalyst.

| SV (Nl/h/kg · cat) | 2000 | 5000 | 10000 | 15000 | 20000 |
|---|---|---|---|---|---|
| MeOH (inlet, g/h) | 4.616 | 11.6220 | 22.8490 | 34.0940 | 45.7280 |

TABLE 9-continued

Effect of Space Velocity (SV) with post hydrogenation on the higher alcohols production: T = 300° C., H2/CO = 0.5, 100 bar, 20 g higher alcohols + 20 g hydrogenation catalyst.

| CO % conversion | 27 | 24 | 17 | 15 | 12 |
|---|---|---|---|---|---|
| Exit composition (g/h/g · cat) | | | | | |
| Methanol | 0.3231 | 0.8962 | 1.7466 | 2.1461 | 2.6456 |
| Ethanol | 0.0093 | 0.0227 | 0.0454 | 0.0801 | 0.0976 |
| 1-Propanol | 0.0138 | 0.0248 | 0.0364 | 0.0539 | 0.0595 |
| 2-Propanol | 0.0034 | 0.0056 | 0.0058 | 0.0095 | 0.0090 |
| 2-Methyl-1-propanol | 0.0265 | 0.0003 | 0.0005 | 0.0012 | 0.0014 |
| Other butanols | 0.0042 | 0.0087 | 0.0136 | 0.0240 | 0.0273 |
| Pentanols | 0.0100 | 0.0157 | 0.0214 | 0.0298 | 0.0516 |
| Hexanols and higher | 0.0086 | 0.0150 | 0.0166 | 0.0283 | 0.0143 |
| Total (Ethanol and higher) | 0.0758 | 0.0928 | 0.1395 | 0.2267 | 0.2608 |

The invention claimed is;

1. Process for the preparation of ethanol and/or higher alcohols comprising the steps of:
   (a) providing an alcohol synthesis gas comprising carbon monoxide and hydrogen in a molar ratio of higher than 0.5;
   (c) adding an amount of methanol and/or higher alcohols to the synthesis gas to obtain a synthesis gas mixture,
   (d) converting the synthesis gas mixture from step (c) in presence of one or more catalysts catalysing the conversion of the synthesis gas mixture into a ethanol and/or higher alcohols containing product; and
   (e) withdrawing the product from step (d), wherein the synthesis gas is purified by removing metal carbonyl compounds prior or after the addition of methanol and/or higher alcohols to the synthesis gas, wherein the metal carbonyl compounds are removed from the synthesis gas by contacting the gas with a sorbent comprising copper aluminium spinel being modified by reduction in a reducing atmosphere at a temperature of between 250° C. and 500° C. prior to being contacted with the synthesis gas.

2. Process of claim 1, wherein the one or more catalysts in step (d) comprise copper, zinc oxide and aluminium oxide and are optionally promoted with one or more metals selected from alkali metals, basic oxides of earth alkali metals and lanthanides.

3. Process of claim 1, wherein the sorbent comprises copper in excess to the amount of copper contained in the copper aluminum spinel.

4. Process of claim 1, wherein the sorbent is arranged on top of a fixed bed of the one or more catalysts catalysing the conversion of the synthesis gas mixture.

5. Process of claim 1, wherein the reducing atmosphere is synthesis gas diluted with an inert gas.

6. Process of claim 1, wherein the conversion of the synthesis gas mixture is performed at a pressure of between 2 and 15 MPa and a temperature of between 270° C. and 330° C.

7. Process of claim 1, comprising the further steps of:
   (f) cooling the withdrawn product in step (e); and
   (g) contacting the cooled product with a hydrogenation catalyst.

8. Process of claim 7, wherein the product in step (f) is cooled to a temperature of between 20° C. and 200° C.

9. Process of claim 7, wherein the hydrogenation catalyst comprises copper, zinc oxide and aluminium oxide.

10. Process of claim 7, wherein the hydrogenation catalyst comprises platinum and/or palladium.

* * * * *